United States Patent [19]

Collier et al.

[11] Patent Number: 5,104,231
[45] Date of Patent: Apr. 14, 1992

[54] VORTEX MIXER DRIVE

[75] Inventors: Charles F. Collier, Wilmington, Del.; James D. Riall, Elkton, Md.

[73] Assignee: E. I. Du Pont de Nemours and Company, Wilmington, Del.

[21] Appl. No.: 736,177

[22] Filed: Jul. 26, 1991

[51] Int. Cl.$^5$ .............................................. B01F 11/00
[52] U.S. Cl. ........................................ 366/208; 74/86; 422/99
[58] Field of Search ............... 366/208, 209, 210, 211, 366/213, 216, 110, 111, 112, 601, 219, 237; 422/99, 104; 74/111, 116, 126, 125.5, 23, 24, 86

[56] References Cited

U.S. PATENT DOCUMENTS

| | | | |
|---|---|---|---|
| 3,090,641 | 5/1963 | Eminger | 74/23 |
| 3,850,580 | 11/1974 | Moore et al. | 23/259 |
| 4,555,183 | 11/1985 | Thomas | 366/208 |
| 4,661,408 | 4/1987 | Lau et al. | 428/405 |
| 4,807,452 | 2/1989 | Brenner | 74/23 |
| 4,834,548 | 5/1989 | Tempel | 366/208 |
| 4,848,917 | 7/1989 | Benin | 366/208 |
| 4,895,453 | 1/1990 | Devlin et al. | 366/219 |

OTHER PUBLICATIONS

Wada et al., Rev. Sci. Instru., 54 (11), pp. 1569-1572 (Nov., 1983).

Primary Examiner—Robert W. Jenkins

[57] ABSTRACT

An apparatus for providing linear motion in two opposed directions and circular motion in a first direction using a single drive motor.

9 Claims, 4 Drawing Sheets

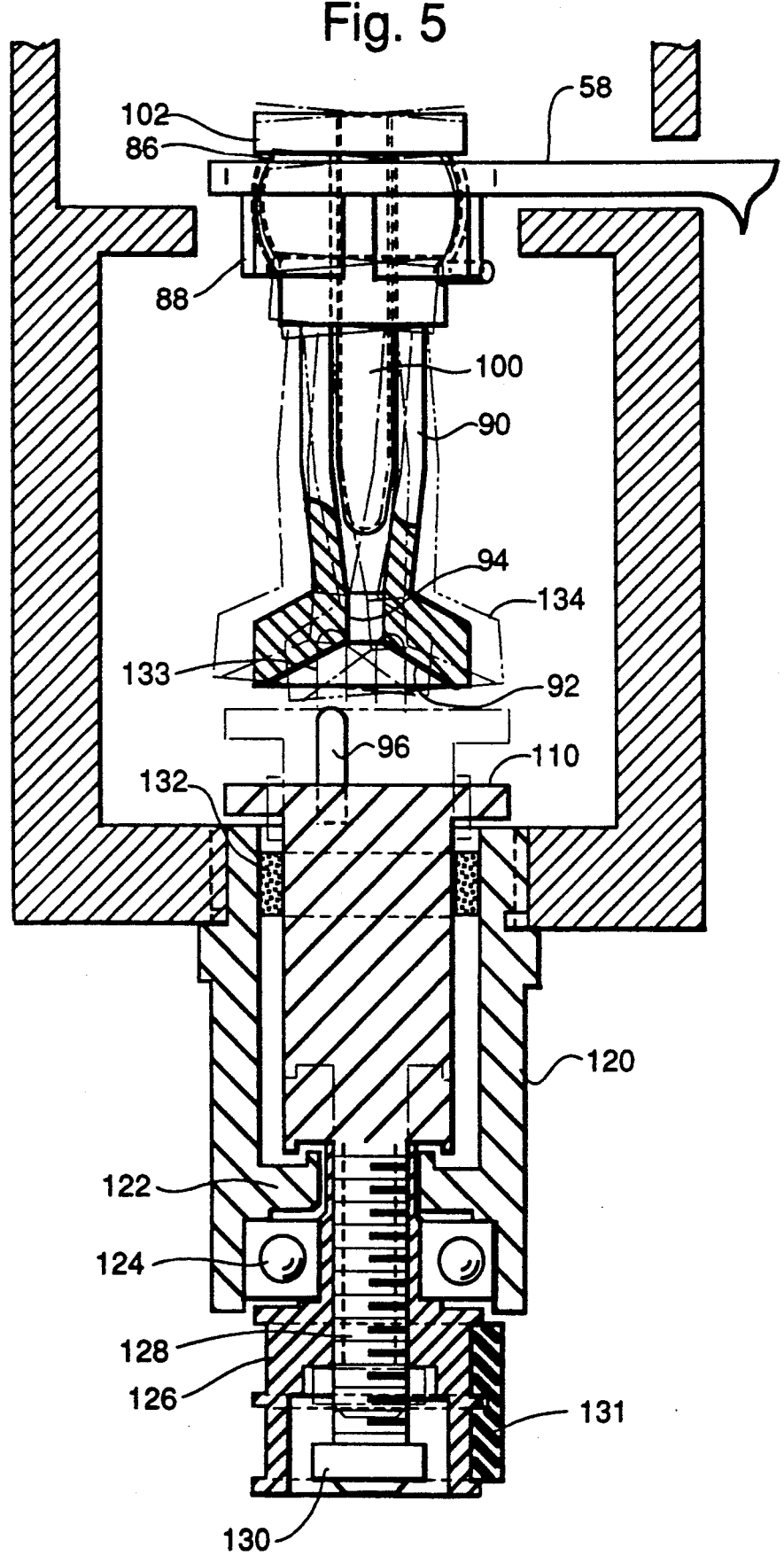

VORTEX MIXER DRIVE

FIELD OF THE INVENTION

This invention relates to a simplified apparatus for establishing a vortex in liquid material held in a container.

BACKGROUND OF THE INVENTION

It is known that creating a vortex in fluids contained in a vessel is an effective means for mixing the fluid. Common laboratory vortexers use a support cup or a resilient vessel and engage the bottom of the vessel with a receiving surface mounted eccentrically to a motor. This translates the lower end of the vessel in a circular path or orbit at a high speed and thereby creates an effective vortex in the fluid contained in the vessel. Exemplary of this type of device are those disclosed in U.S. Pat. Nos. 4,555,183 (Thomas) and 3,850,580 (Moore et al.). These devices are manual in that an operator is required to hold the vessel in contact with the eccentrically movable means to create the vortex in the fluid disposed in the vessel.

Such vortex type devices would be extremely advantageous if used in an automated chemical analysis instrument as it is noninvasive and therefore can avoid the concern of contamination associated with an improperly cleaned invasive mixing means.

A device that incorporates this type of mixing into an automated testing apparatus is disclosed in an article by Wada et al. entitled "Automatic DNA Sequencer: Computer-programmed Microchemical Manipulator for the Maxam-Gilbert Sequencing Method", Rev. Sci. Instrum. 54(11), November 1983, pages 1569-1572. In the device disclosed in this article, a plurality of reaction vessels are held flexibly in a centrifuge rotor. A rotational vibrator is mounted on a vertically moving cylinder. When mixing is desired, the reaction vessel is positioned in a mixing station directly above the rotational vibrator. The vertically movable cylinder is moved upwardly to contact the bottom of the reaction vessel with a rotary, vibrating rubber portion. The rotational vibrator is then actuated to create the vortex in the fluid contained in the vessel.

This device has the shortcoming that two degrees of motion are required to create a vortex in a reaction vessel located at a mixing station the rotary motion of the vibrator and the linear motion of the vertically moving cylinder. This requires two separate actuators as well as the additional position sensors and software to properly control them. These extra elements equate to an inherently greater cost and lower reliability than a device that could perform the same function utilizing a single degree of motion.

This is of particular significance in a serial processing chemical analysis instrument in which a plurality of mixing stations are required. In serial instruments, reaction vessels are stepped or indexed through various processing positions such as add sample and/or reagent incubate, wash, mix, etc. Such mixing is desirable in most automated chemical analyzers and can become necessary when solid supports such as glass beads or magnetic particles are used that often have a tendency to sink to the bottom of the reaction vessel.

For example, in heterogeneous immunoassays, magnetic particles can be used as the basis for separation of reagents from ligand-antibody bound particles. A particularly desirable particle is disclosed in U.S. Pat. No. 4,661,408 (Lau et al.). These particles have a tendency to settle at a rate which can be detrimental to the kinetics of the reaction. It is therefore desirable that the reaction mixture be mixed regularly during incubation while the reaction is occurring. One mixer that overcomes many of the disadvantages of the prior art is that described in U.S. Pat. No. 4,848,917 issued July 18, 1989 to E. I. du Pont de Nemours and Company. This patent describes a vortexing mixer drive that has a rotatable coupling rod where an end face defines an off center countersink with a bore at the center of the countersink. The rod is actually displaced to engage a vessel's protuberant tip to effect rotational motion and thereby nutate the material with the vessel. The disadvantage of this system is that it takes two translators, a rotary translator as well as a linear translator.

Another system is that described in U.S. Pat. No. 4,895,453 issued Jan. 23, 1990 to Devlin et al. This system describes an automatic vortexing drive in which a rotatable coupling has a cuplike recess positioned off of an opening radially outward from the axis of rotation of the coupling. The coupling is positioned to intercept at the lower and reaction vessels in the recess. Selective rotation of the coupling permits the vessels to pass the coupling or be engaged by the coupling and mutated. This system while quite excellent requires somewhat complex controls of the drive mechanism.

Many of these prior art systems in general are seen to have a number of disadvantages; one is that they tend not to be simple and require either a large number of parts or a complex drive system or multiple drive motors. Another is in some cases they do not gently engage the vessels which are to be nutated sometimes causing spillage of the contents of the vessels. Finally, the systems of the prior art do not always reliably engage the vessels to be nutated.

SUMMARY OF THE INVENTION

Many of these advantages of the prior art devices are overcome in accordance with this invention by utilizating an apparatus that provides bidirectional linear motion and single directional rotational motion using a single drive motor. This system includes a base, a nut rotatably mounted in the base, adapted to be rotated by the motor in opposite directions, a screw engaged in the nut, a driven member mounted to one end of the screw, limit means on the other end of the screw opposite the one end to limit its movement in a first linear direction, and braking means cooperating with the driven member to impede rotation of the screw, whereby rotation of the nut in a first rotational direction displaces the driven member in a first linear direction until limited by the limit means and then rotates the driven member in the first rotational direction and rotation of the nut in a second rotational direction opposite the first displaces the driven member in a second linear direction opposite the first.

In a preferred embodiment of this apparatus the braking means is a friction spring mounted on the base and frictionally engaging the driven member. Also the limit means may be a disk mounted on the end of the screw opposite the one end, thereby to engage the nut when the limit is reached.

Using this bidirectional linear motion and single directional rotational motion, an apparatus may be provided for establishing a vortex in liquid materials adapted to be contained in elongated compartments, each compartment having a longitudinal axis, disposed on a transport, comprising: a plurality of compartments carriers disposed on the transport, each carrier adapted to hold flexibly the upper portions of the compartment, the transport having a path of movement each compartment's lower portion having a coupling means along the longitudinal axis, a rotatable drive coupling means, having an axis of rotation, a mixing face transverse to the axis of rotation, and located under a region in the path of movement of the transport and compartment carriers, operating to displace the mixing face to engage the compartment coupling means off of the axis of rotation, whereby rotation of the mixing face can establish a vortex in the liquid materials, the drive coupling means having a base, a rotatably mounted nut in the base, a screw engaged in the nut and defining the axis of rotation, the mixing face mounted to the upper end of the screw, and means located on the bottom end of the screw to limit its upward movement, means to frictionally limit rotation of the mixing face, and means to reversibly rotate the nut, thereby to drive the mixing face up to engage and rotate the coupling means when the nut is rotated in a first direction and conversely disengage the coupling means when the nut is rotated in a second direction opposite the first direction.

This apparatus is quite simple and has a relative small number of parts. It utilizes a single drive motor which permits the screw to be not only lifted but also spun to create the nutational motion in the reaction vessel. It very gently engages the reaction vessel to be spun so as to reduce the opportunity for spillage therein. It also reliably engages the bottom of the reaction vessel.

BRIEF DESCRIPTION OF THE DRAWINGS

The present invention may be more fully understood from the following detailed description thereof taken in connection with the accompanying drawings which form a part of this invention description and in which similar reference numerals refer to similar elements of all figures of the drawings, in which:

FIG. 5 is a cross sectional view of a vortexing drive mechanism constructed in accordance with this invention adapted to nutate a reaction vessel.

DETAILED DESCRIPTION OF THE PREFERRED EMBODIMENT

Figure 1:
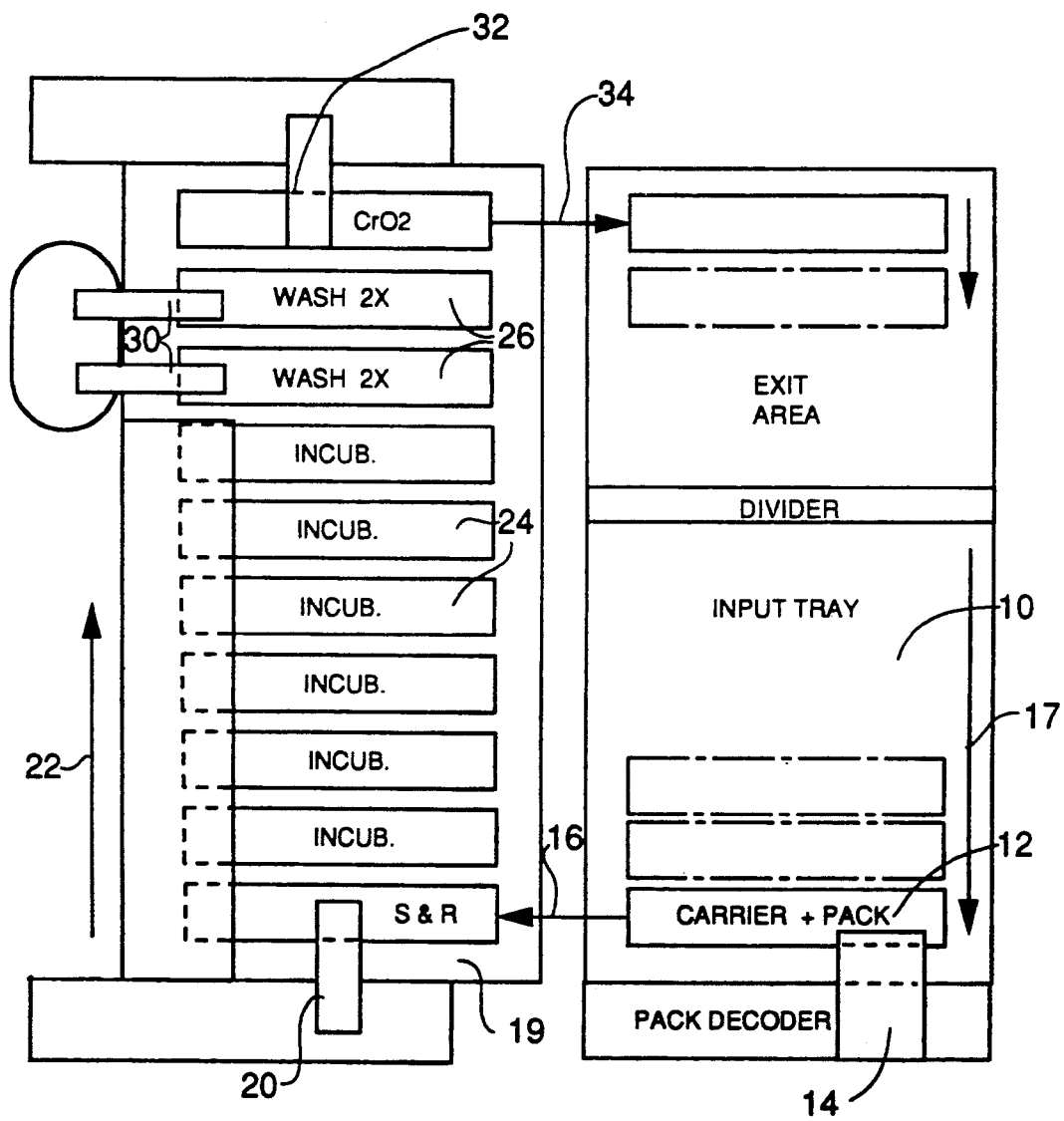
FIG. 1 is a diagrammatic representation of a chemical analyzer designed to do immunoassays which contain magnetic particles requiring periodic vortexing during the reaction period.

As may be seen in FIG. 1, there is a block diagram illustrating an analyzer in which the apparatus of this invention. The analyzer has an input or inlet chamber 10 in which there are held a plurality of carriers 12. Each carrier 12 holds a sample holder for a sample to be processed and a flexibly mounted reaction vessel. There are magnetic particles in the reaction vessel, i.e., particles that are responsive to a magnetic field, along with reagents for performing immunoassays. The carrier also holds a transparent removable container that is introducible into another instrument for evaluating the processed immunoassay reaction. An optical decoder 14 is positioned at the lower portion of the inlet chamber (in the drawing) for decoding a code on the sample holder in the carrier which will identify the sample and the particular test to be run so that the analyzer may be actuated properly.

A first transport 18 moves the carrier 12 linearly in a first direction and urges the carriers against the decoder 14. Once decoded, a shuttle mechanism 16 transports the carriers linearly in a second direction transverse to the first direction from one end of the inlet chamber to one end of a processing chamber 19. The processing chamber 19 is generally parallel to the inlet chamber and is so positioned to minimize the space occupied by the entire processing unit. A first translator symbolized by the block 20 acts on each carrier 12 to transfer each carrier's sample and reagents into the carrier's reaction vessel. A transport mechanism 22 sequentially transports the carriers 12 linearly in a third direction opposite to and generally parallel to the first direction to several processing positions 24. At the second, fourth and sixth processing positions 24 are means of vortexing each carrier's reaction vessel. At the eighth and ninth processing positions, wash means 26 are provided for removing liquids from each carrier reaction vessel and replacing the liquids with a different liquid. Translating means 30 are provided at each wash position to apply a magnetic field to each carrier reaction vessel prior to removal of the liquid so as to position the magnetic particles against walls of the reaction vessel.

Finally, a second translating means 32 at the last processing position transfers the contents of each carrier's reaction vessel into its container for storage until analyzed. A fourth transport means 34 transports each carrier 12 transversely of the third direction from the processing chamber back into the other end of the inlet chamber. Finally, a fifth means 36 operates to transport each carrier 12 from the other end of the inlet chamber 10 in a direction generally parallel to the first direction for storage. Following storage, the carriers 12 may be removed at will so that the container can be removed therefrom and put into a suitable analyzer for analysis such as the aca ® Clinical Analyzer sold by E. I. du Pont de Nemours and Company, Wilmington, DE.

Figure 2:
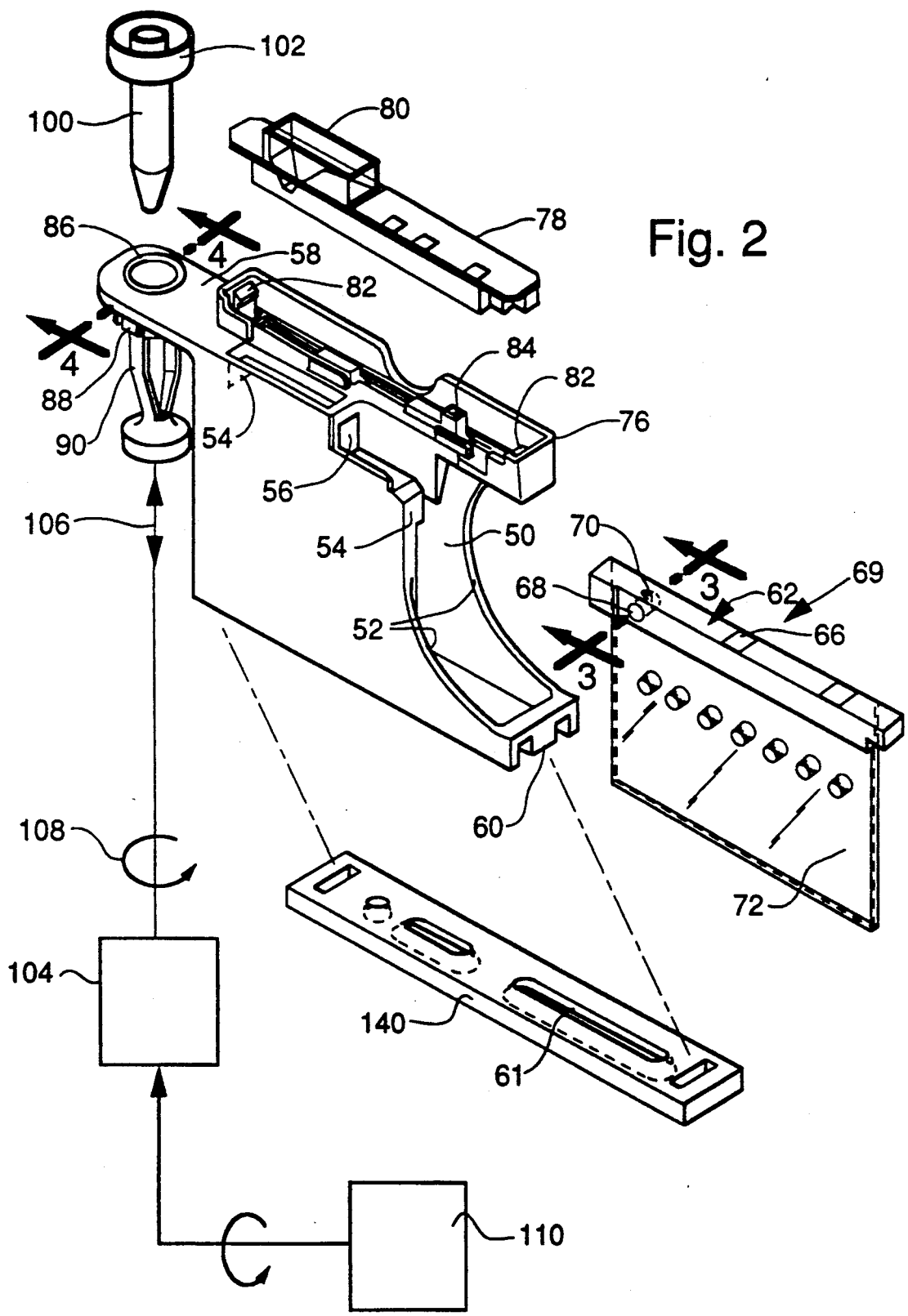
FIG. 2 is an exploded view of one of the carriers depicted in FIG. 1 that is used to hold a reaction vessel that needs vortexing.
Figure 3:
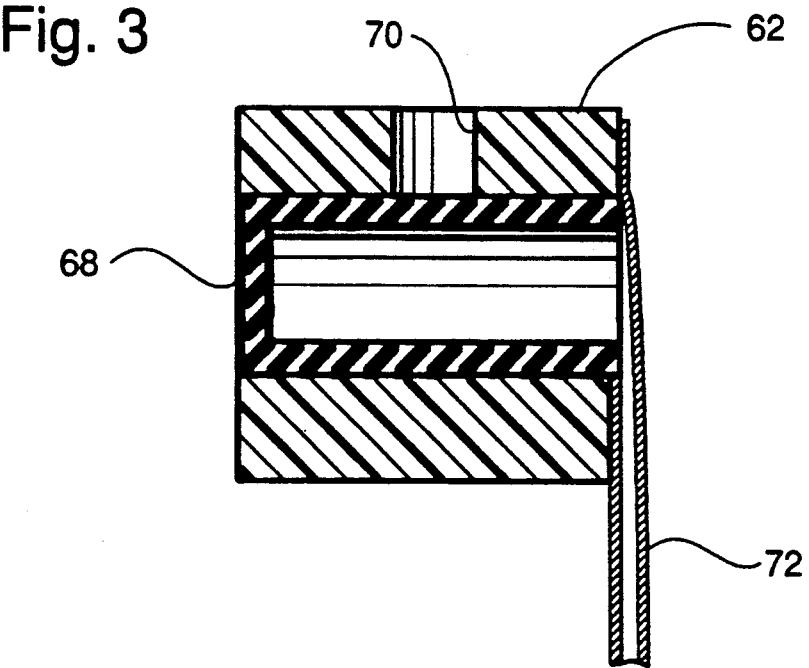
FIG. 3 is a sectional view taken along the section lines 3—3 of FIG. 2.
Figure 4:
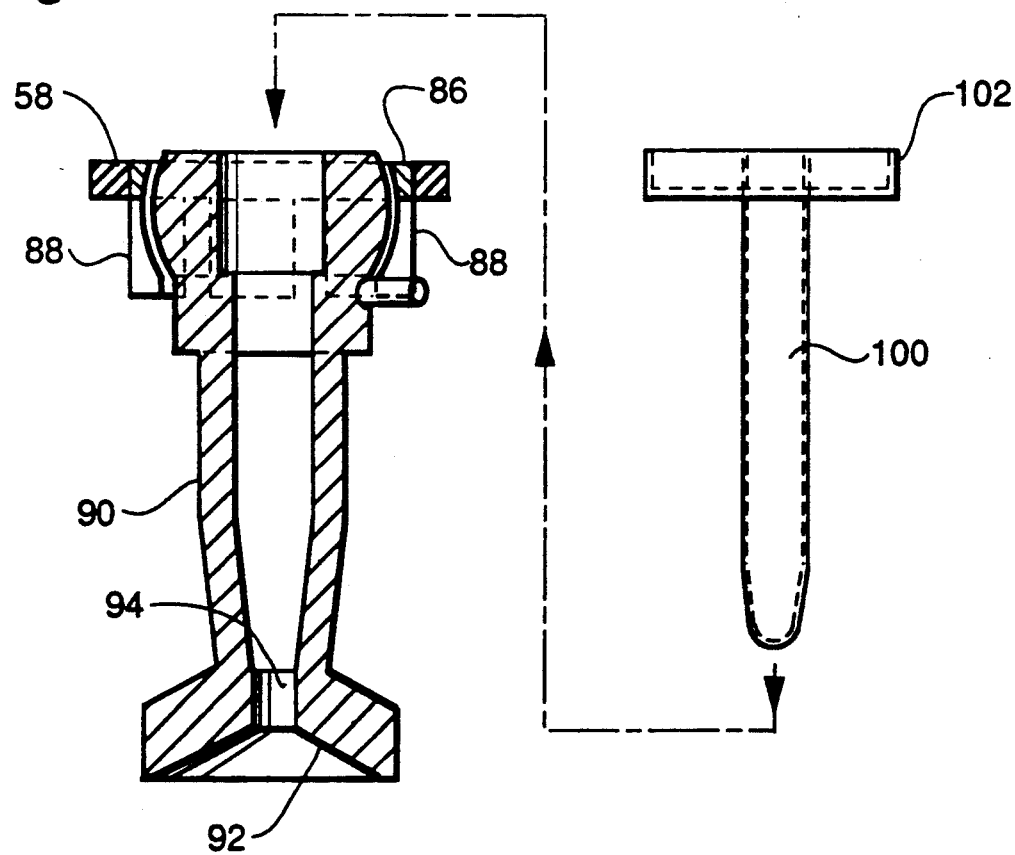
FIG. 4 is a sectional view taken along the section lines 4—4 of FIG. 2.

There may be seen in FIGS. 2, 3, and 4 exploded sectional views of one of the carriers 12 of FIG. 1. The carrier is seen to contain a hollow, molded housing 50 defined by a pair of sidewalls 52, a top plate 58, and a base support 60. A drive bar 140 is positioned in the lower portion between the sidewalls 52 and is secured to the base support as by gluing. This bar has receptacles to facilitate its receiving drive pins for positioning the bar 140 and hence the carrier. The housing may be formed of polysulfone or any other suitable engineering plastic which is rigid, strong and chemically inert. Attached to the front sidewall (in the drawing) is a partition 54 which cooperates with the top 58 to accommodate the top frame of an analytical pack 62 of an analytical pack 64 which may be the same and preferably is the same as the aca ® pack used in the aca ® Automatic Clinical Analyzer sold by E. I. du Pont de Nemours and Company, Wilmington, Delaware U.S.A. The aca ® pack has identifying indicia 66 on the top which may be read by appropriate sensors to indicate the particular test being run and includes a septum 68 with an orifice 70 which may be used to introduce materials into a plastic pack 72. Since the aca ® pack is well known it will not be described further.

In any event, the partition 54 and top 58 cooperate to define an orifice 56 adapted to accommodate the top member of the aca ® pack 62 so it may be inserted into the carrier with the lower side pack 72, which is formed of plastic material. The side pack is to slide in between the two walls 52. The top of the carrier 50 also includes an elongated cuplike member 76 which is adapted to receive a removable sample reservoir 78 containing a reservoir 80. The sample reservoir 78 is held in the position within the opening 76 by appropriate molded grips 82. A fitting feature 84 to control access to the opening may be provided for the sample holder 78.

To complete the carrier 50, the end of the top member 58 may have an orifice 86 with downwardly extending flanges 88 adapted to hold a reaction vessel holder 90. The flanges 88 are concave on the inside to define a socket which compensates with the bulbous top on a reaction vessel 90 in a ball and socket joint manner. The lower portion of the reaction vessel holder 90 may be shaped as depicted in FIG. 5 to have an inverted cavity or receptacle 92 at the upper end of which is hole 94 adapted to receive a pin 96 from a drive member, as will be described.

In an alternative embodiment of this invention, the reaction vessel holder 90 may be the reaction vessel itself although the use of the holder is preferred for its long term stability and reliability. If the reaction vessel 90, as a tube holder, is adapted to receive a reaction vessel 100, the vessel has at the upper portion thereof a concentric chamber 102 for holding reaction reagents that typically may be used, for example, in an immunoassay process.

The reaction vessel holder 90 may be positioned in a thermal chamber 59 and is driven or nutated by an automatic 104 constructed in accordance with this invention and shown in detail in the cross sectional view of FIG. 5. This drive apparatus mounted to the bottom of the thermal chamber 59 and provides a bidirectional motion as depicted by the line 106 (FIG. 2) as well as rotational motion as depicted by the line 108 to the reaction vessel holder 90. This drive apparatus is powered by a single bidirectional drive motor 110 which provides rotational motion to the drive apparatus 104. The automatic apparatus engages the reaction vessel holder 90 by elevating a mixing cylinder or plate on which the pin 96 is positioned contiguous the periphery at a point off of the elongated axis of the mixing plate. In other words the pin 96 engages the bottom end of the mixing vessel 90 into a position which is eccentric to the axis which mounts the mixing plate 110. The apparatus then spins the plate moving the engaged end of the vessel to an orbit. If the vessel is managed so that it is free in two rotational directions of freedom, then the contents of the reaction vessel holder 90 will swirl or nutate thus mixing them. Reversal of the drive which spins the mixing cylinder or plate 110 stops the orbiting of the vessel and lowers the cylinder or plate thus disengaging the pin 96 from the reaction vessel holder 90.

In accordance with this invention the drive 104 has a cylindrical housing or base 120 (FIG. 5) which has an internal flange 122 for mounting a bearing 124 which in turn mounts a nut 126. The lower end (in the drawing) of the nut 126 is shaped to be cylindrical and hollow to accommodate a screw 128 which is threaded through the nut. At the top end of the screw is formed an elongated cylindrical shaped mixer which defines a mixing cylinder 110 which as described mounts the eccentrically located pin 96. The lower end of the screw 128 has a locknut 130 engaged thereon to limit the upper travel of the screw 128 in the nut 126.

Rotation of the mixing cylinder 110 is prevented by a leaf spring type clamp 132, only a portion of which is shown, which engages the periphery of the mixing cylinder 110 to inhibit its motion up to a degree. The leaf spring 132 is mounted to the housing 120. The lower portion of the nut 126 is shaped to have the form of a drive pulley to accommodate a drive belt 131 from a motor 110 (FIG. 2).

This automatic apparatus functions by rotating the nut 126 with a drive belt attached to the pulley 126. The leaf spring 132 mounted on the base drags on the outside diameter of the mixing cylinder 110 and thereby acts as a rotational clutch to the screw and mixing cylinder. When the nut is thus rotated, the clutch prevents the screw from rotating so instead the screw elevates the mixing cylinder 110. This elevation continues until further elevation is prevented by the locknut 130 at the bottom of the screw. At this point the clutch then slips allowing the nut 126, screw 128, mixing cylinder 110 and locknut 130 to rotate together. By this time, the pin 96 has risen (dashed line 133) to engage the recess and ultimately the hole 94 in the mixing vessel holder 90.

The engagement is complete when the screw reaches the top of the travel and thereafter the eccentric motion of the pin 96 causes the bottom of the mixing vessel holder to rotate as depicted by the dashed line 134 and thereby causing vortexing to occur in the mixing vessel. If the rotation of the nut is reversed the sequence starts over but in the opposite direction, i.e., the screw 128 is lowered until it strikes the screw 126.

This invention is seen to be very advantageous. It functions with a small number of inexpensive parts. One drive motor permits the lifting and spin of the mixing cylinder. The device lends itself to be used with any number of duplicate devices and all to be driven by the same drive. It engages the bottom of the mixing vessel holder or mixing vessel gently so as to avoid on spilling of the vessel contents. Furthermore the engagement of the pin 96 in the hole 94 is a very positive, reliable drive even if one of the vessels is mispositioned.

We claim:

1. An automatic apparatus for establishing a vortex in liquid materials adapted to be contained in elongated compartments, each compartment having a longitudinal axis, disposed on a transport, comprising:

a plurality of compartments carriers disposed on the transport, each carrier adapted to hold flexibly the upper portions of the compartment, the transport having a path of movement, each compartment's lower portion having a coupling means along the longitudinal axis, a rotatable drive coupling means, having an axis of rotation, a mixing cylinder transverse to the axis of rotation, and located under a region in the path of movement of the transport and compartment carriers, operating to displace the mixing cylinder to engage the compartment coupling means off of the axis of rotation, whereby rotation of the mixing cylinder can establish a vortex in the liquid materials, the drive coupling means having a base, a rotatably mounted nut in the base, a screw engaged in the nut and defining the axis of rotation, the mixing cylinder mounted to the upper end of the screw, and means located on the bottom end of the screw to limit its upward movement, means to frictionally limit rotation of the mixing cylinder, and means to reversibly rotate the nut, thereby to drive the mixing cylinder up to engage and rotate the coupling means when the nut is rotated in a first direction and conversely disengage the coupling means when the nut is rotated in a second direction opposite the first direction.

2. The automatic apparatus of claim 1 wherein the coupling means define an open receptacle.

3. The automatic apparatus of claim 2 wherein the mixing face defines a pin located off the axis of rotation adapted to engage the receptacle.

4. The automatic apparatus of claim 3 wherein the receptacle defines a recess adapted to receive the pin.

5. The automatic apparatus of claim 4 wherein the friction means forms a guide support for the mixing cylinder.

6. An apparatus for providing bidirectional linear motion and single directional rotational motion using a single drive motor comprising:

a base, a nut rotatably mounted in the base, adapted to be rotated by the motor in opposite directions, a screw engaged in the nut, a driven member mounted to one end of the screw, limit means on the other end of the screw opposite the one end to limit its movement in a first linear direction, and braking means cooperating with the driven member to impede rotation of the screw, whereby rotation of the nut in a first rotational direction displaces the driven member in a first linear direction until limited by the limit means and then rotates the driven member, in the first rotational direction and rotation of the nut in a second rotational direction opposite the first displaces the driven member in a second linear direction opposite the first.

7. The automatic apparatus of claim 6 wherein the braking means is a friction spring mounted on the base and frictionally engaging the driven member.

8. The automatic apparatus of claim 7 wherein the limit means is a disk mounted on the end of the screw opposite the one end, thereby to engage the nut when the limit is reached.

9. The automatic apparatus of claim 6 wherein the limit mean is the cylinder mounted on the end of the screw opposite the one end, thereby to engage the nut when the limit is reached.

* * * * *